United States Patent [19]

Froehlich et al.

[11] Patent Number: 5,359,184
[45] Date of Patent: Oct. 25, 1994

[54] OPTICAL ENCODING UTILIZING SELECTIVELY REFRACTED LIGHT

[75] Inventors: John A. Froehlich, West Readding, Conn.; Eric S. Anderson, Pleasantville, N.Y.

[73] Assignee: Medical Laboratory Automation, Inc., Pleasantville, N.Y.

[21] Appl. No.: 790,685

[22] Filed: Nov. 8, 1991

Related U.S. Application Data

[62] Division of Ser. No. 272,159, Nov. 16, 1988, Pat. No. 5,098,661.

[51] Int. Cl.$^5$ ............................................. G06K 7/10
[52] U.S. Cl. ................................... 235/454; 235/494
[58] Field of Search .............. 235/454, 494, 487, 490, 235/470; 250/223 B

[56] References Cited

U.S. PATENT DOCUMENTS

| | | | |
|---|---|---|---|
| 4,201,338 | 5/1980 | Keller | 250/223 B |
| 4,211,918 | 7/1980 | Nyfeler et al. | 235/454 |
| 4,266,122 | 5/1981 | Schmidhauser | 235/454 |
| 4,371,498 | 2/1983 | Scordato et al. | |
| 4,376,887 | 3/1983 | Greenaway et al. | 235/454 |
| 4,625,101 | 11/1986 | Hinks et al. | 235/454 |
| 4,906,829 | 3/1990 | Iseli | 235/454 |

*Primary Examiner*—Robert A. Weinhardt
*Attorney, Agent, or Firm*—Wolf, Greenfield & Sacks

[57] ABSTRACT

Optical encoding of a cuvette or other object is provided by means of multiple facets molded integrally into flanges or other portions of the object, which facets selectively refract light passing therethrough in accordance with a predetermined code. The detector for the coded light includes a separate detector for each code state of the facets, with the detector having a different output when no facets are between a light source and the detectors. The facets are preferably bevels, which are selectively angled in accordance with the code.

15 Claims, 3 Drawing Sheets

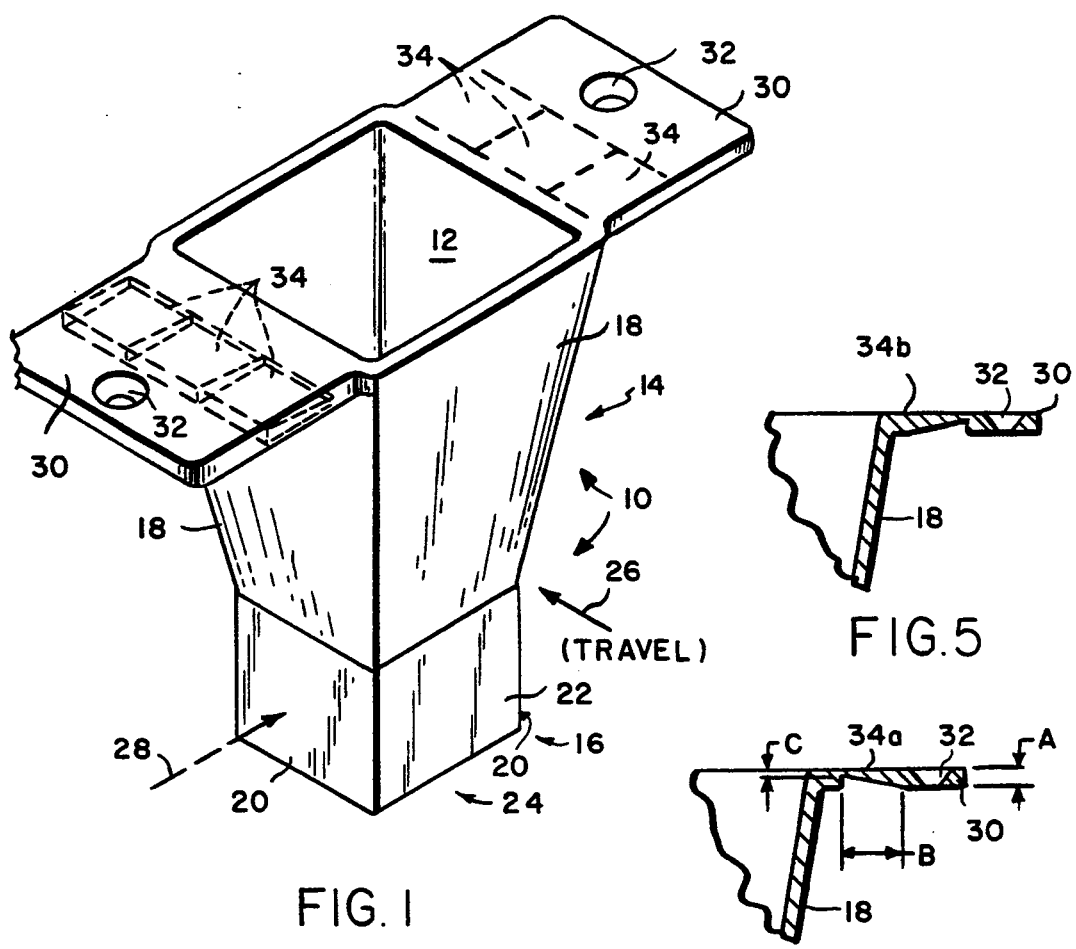
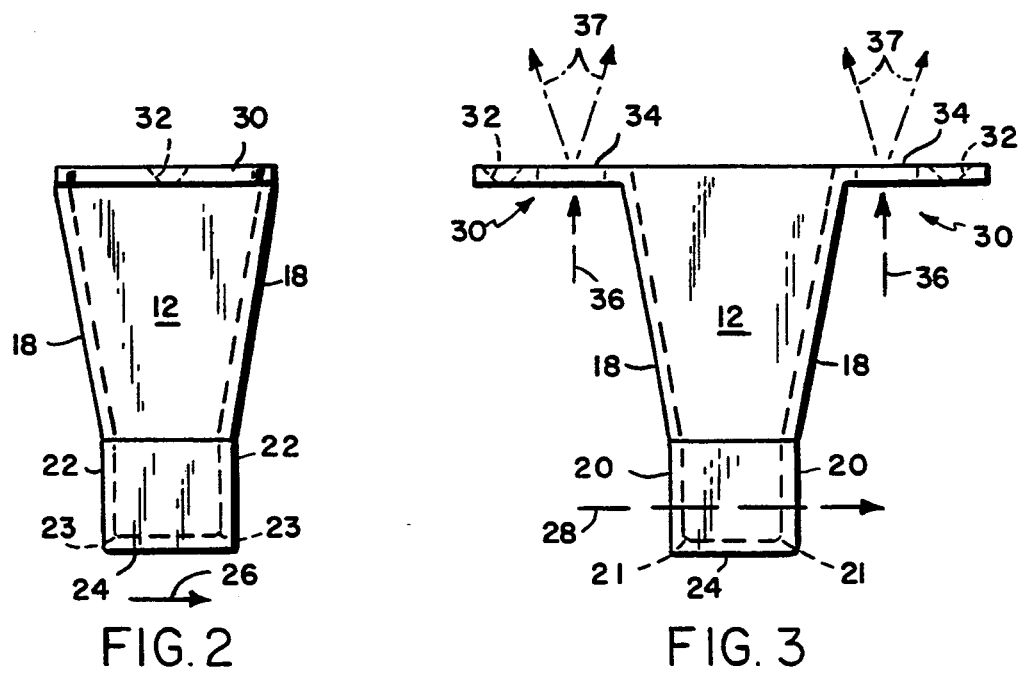

OPTICAL ENCODING UTILIZING SELECTIVELY REFRACTED LIGHT

This is a divisional of application Ser. No. 07/272,159, filed on Nov. 16, 1988, now U.S. Pat. No. 5,098,661, issued Mar. 24, 1992.

FIELD OF THE INVENTION

This invention is related to containers or cuvettes for holding samples to be tested, and more particularly to cuvettes having optically readable codes for use in automated testing apparatus.

BACKGROUND OF THE INVENTION

Automated testing of biological samples is becoming more prevalant. For example, automated testing apparatus for photometrically determining coagulation time and other blood parameters are disclosed in U.S. Pat. Nos. 3,969,079, 3,607,099, and 3,718,439. In these instruments, a sample is placed into a cuvette, after which the testing instrument automatically dilutes the sample and adds reagents as necessary to perform the test. After the sample has been so treated, the cuvette is moved into position so that an optical beam from a light source passes through the sample and impinges upon a photodetector which provides an output representative of the optical density of the sample. By suitably processing and measuring the photodetector output, various parameters may be determined. The techniques for performing such tests are well known, as exemplified by the above referenced patents.

The design of cuvettes for use in such apparatus is important to achieving optimum performance from the apparatus. Proper design increases the accuracy of the measurement. Operator errors may be minimized by providing the cuvettes with coding to automatically inform the testing instrumentation of the test to be performed.

Many different cuvette designs have been developed over the years. See for example, U.S. Pat. Nos. 3,905,772, 4,119,407, 4,251,159, and 4,371,498. In the last mentioned patent, a cuvette having dual receptacles is described. The cuvette further includes coding to enable a testing instrument to determine the particular test procedure to be performed on the sample in the cuvette. The cuvette is encoded by means of one or more holes placed in the top section of the cuvette. These holes may be sensed by solenoid operated probes in the testing instrument to decode the cuvette. This method, while successful, had drawbacks, including contamination of the probes requiring frequent maintenance, and the necessity of making the cuvette walls thick enough to withstand the force of the mechanical probe.

Due to various considerations, discussed in more detail below, the walls of cuvettes for blood testing must be as thin as practical. Because of this, optically encoding cuvettes has posed problems. Cuvettes are typically made from plastic materials. In order to avoid contaminating samples and increasing costs, it is undesirable to apply extraneous materials, such as labels or reflectors, to the cuvettes. Due to the thinness of the cuvette walls, it is difficult to make sections of a cuvette opaque enough, for example by roughening the surface, to be reliably detected by a photo-optical detector.

SUMMARY OF THE INVENTION

The present invention includes a novel cuvette design in which a cuvette is encoded by means of molded facets which refract a light beam to provide for optical detection of a code. When made from a plastic, such as polystyrene, extremely thin walls may be provided for the cuvette while still providing sufficient refraction through the facets to reliably encode the cuvette.

The cuvette includes a receptacle having flanges on either side in which the facets are molded. The flanges additionally include locating holes to allow the testing instrument to precisely position the cuvette for photometrically measuring the sample being tested. The flanges are slightly flexible which provides enhanced positioning capabilities. Single and dual cuvette embodiments are described.

Electronic circuitry for detecting the code provided by the facets is described. The circuitry can be provided with means for discriminating against ambient light. An alternate method of providing cuvette encoding by means of cylindrical lenses molded into the flange is also disclosed.

BRIEF DESCRIPTION OF THE DRAWINGS

The present invention is explained below by means of example with reference to the following figures of which:

FIG. 1 is an isometric view of a single cuvette;

FIGS. 2 and 3 are side views of the cuvette of FIG. 1;

FIGS. 4 and 5 show details of facets molded into the cuvette flange;

DESCRIPTION OF THE PREFERRED EMBODIMENT

Figure 6:
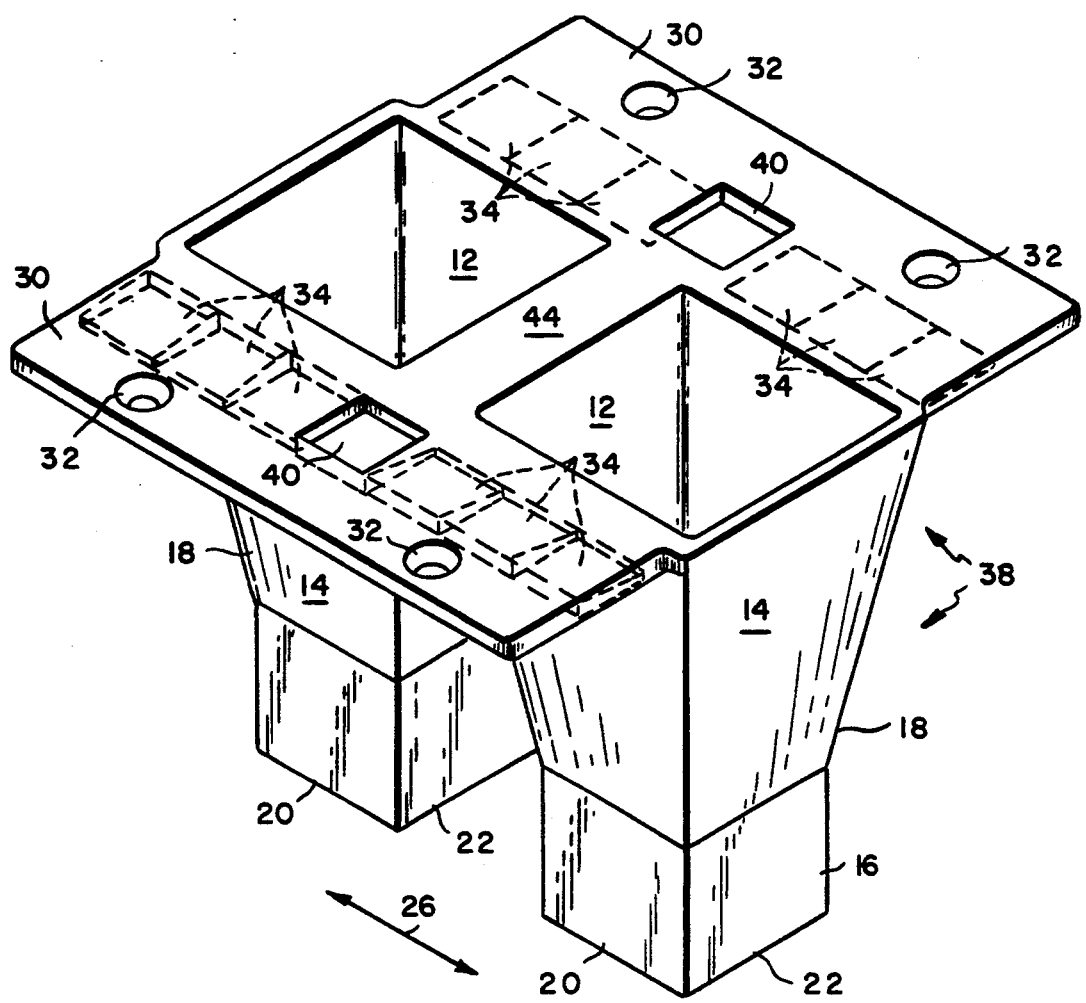
FIG. 6 is an isometric view of a double cuvette.

Referring to FIG. 1, there is shown an isometric view of a cuvette having a single receptacle for holding a sample. The receptacle 12 is made up of an upper, trapezoidal section 18 and a lower, rectangular section 16. Trapezoidal section 14 is made up of four side walls 18 which slope down at an angle from the top opening of the receptacle 12 to the bottom section 16. The cuvette may be formed of a plastic material, such as polystyrene. In the preferred embodiment, side walls 18 are inclined at an angle of approximately 9.5° with respect to vertical. The opening at the top of trapezoidal section 14 is approximately 0.38 inches on a side, the height of section 14 is about 0.52 inches, and the thickness of walls 18 is 0.025 inches.

At the bottom of trapezoidal section 14 is the lower section 16. The light beam used to perform the photometric analysis of the sample passes through lower section 16, as shown by arrow 28. The light beam direction is perpendicular to side walls 20 which should be substantially parallel to one another. A second pair of side walls 22 are perpendicular to side walls 20. Side walls 20 and 22 are typically 0.025" thick. Walls 20 and 22 may be tilted very slightly outward to aid in releasing the cuvette from the mold when the cuvette is made. The walls 20 and 22 in the described embodiment are angled outward at an angle of about one-half degree.

The cuvette includes a bottom wall 24. Bottom section 14 is approximately 0.2 inches on each side. During the testing procedure, the sample is maintained at a constant temperature by means of a heated block having a flat surface on which the bottom wall 24 of the cuvette rests. It is advantageous to keep bottom wall 24 as thin as possible to maximize the heat transfer through the bottom wall. In the described embodiment, bottom wall 24 is 0.020" thick.

It is desirable that a cuvette be able to perform the tests with as small a sample volume as possible. In the described cuvette, 150 microliters will fill the bottom section 16 of the cuvette so that the light beam can pass through the sample to perform the tests. Some tests, however, require large amounts of dilution or reagents, and larger volumns are required to accommodate these tests. By providing a trapezoidal upper section 14, the total volume of the cuvette may be increased while keeping the height shorter than would be possible if the walls of bottom section 16 were extended vertically. The trapezoidal upper section 14 also contributes some rigidity to the cuvette structure. It is important that diluents and reagents which are dispensed into the cuvette prior to testing not impinge upon the sidewalls of the cuvette, which might decrease the mixing of the sample. For all these reasons, the described shape of the cuvette has advantages over previously used cuvettes. The cuvette described can hold a sample volume of 500 microliters with enough freeboard to minimize the possibility that the sample will spill.

The relationship of the walls of the cuvette may be better seen in FIGS. 2 and 3 which are side views facing respectively walls 20 and 22 of the cuvette. It is important that walls 20 through which the light beam 28 passes be as flat as possible to avoid any optical distortion. Corners 21 between side walls 20 and bottom walls 24 are shown in FIG. 3 and should be made as square as practical. The intersection of side walls 22, which parallel the light path, and bottom wall 24 may be made more rounded as shown at corners 23 in FIG. 2. Rounded corners 23 provide extra strength and serve to reduce somewhat the volume in bottom section 16. In the described embodiment, corners 23 have a radius of approximately 0.06".

During the testing procedure, cuvette 10 moves in a direction parallel to side walls 20 of the cuvette, as indicated by arrow 26 representative of the direction of travel. Sequential cuvettes are moved so as to intersect photometric beam 28 as the sample in the cuvette is tested. It is important that the cuvette be positioned as precisely as possible during the photometric analysis. In the present invention, the cuvette includes two flanges 30 which project from the top of the cuvette to each side of the cuvette. Flanges 30 each include positioning holes 32 located along the outer edges thereof. During the testing procedure, locating pins, not shown, are lowered so as to engage positioning holes 32 to locate the cuvette. Holes 32 are preferably formed in a conical shape. The positioning pins are formed in the shape of complementary cones which engage holes 32. As the locating pins are lowered, the conical surfaces of the pins can move the cuvette in a horizontal plane to compensate for small misalignments in the cuvette positioning by the transport mechanism. The bottom of holes 32 is preferably open, i.e., holes 32 extend completely through flange 30. This allows the conical tips of the locating pins to be pointed to maximize the capture range of the locating pins when aligning the cuvette. In the preferred embodiment, locating holes 32 have a diameter at the top surface of approximately 0.1 inches, and the side walls of holes 32 form an angle of 45° with the top of flange 30. The thickness of flanges 30 is about 0.035 inches in the described embodiment, and the flanges extend about 0.5 inches from side walls 18.

To provide for manufacturing tolerances in the dimensions of cuvette 10 and in the transport and positioning mechanism in the testing instrument, flanges 30 should be slightly flexible so that the locating pins which engage holes 32 may descend sufficiently far to ensure that they are in firm contact with the holes. The locating pins are so designed that they descend far enough to slightly flex flanges in a downward direction when the pins are at their lowest position. This has the advantage that the bottom surface 24 is pressed against the heated block of the instrument to maximize the heat transfer from the block to the sample in the cuvette. In the described embodiment, the flanges can be flexed downward by at least as far as the thickness of the flange, which is about 0.035 inches, at their outside edges when positioned by the locating pins.

The cuvette may be encoded by means of one or more facets 34 which are formed by means of bevels in flange 30. In the cuvette shown in FIG. 1, three facets 34 are formed on each of the two flanges 30 extending laterally from the cuvette, although a larger or smaller number of facets may be used. The facets 34 are formed by means of a bevel molded into one surface of the flange. Preferably, the bevel is formed on the bottom of flange 30.

FIGS. 4 and 5 are sectional views taken through one of the flanges 30 and side walls 18 of the cuvette. In FIG. 4, a bevel 34a is formed in flange 30 as shown. FIG. 5 shows a bevel 34b formed in the opposite direction on the bottom side of flange 30. Bevels 34a and 34b slope in opposite directions, and as described in more detail below, may be easily detected or read by means of a light beam directed through the bevel. A light beam passing through bevels 34 will be refracted sideways by the plastic, due to the increased index of refraction of the plastic material as compared with air. For polystyrene, the index of refraction is about 1.6.

This is illustrated in FIG. 3. A light beam 36 directed through bevels 34 is refracted in the direction of the bevel and will emerge from the top section of flange 30 at an angle to vertical as shown by arrows 37. The angle of the deflected beam may be detected by photodiodes or other means to provide an electrical indication of the angle of the bevel. It is preferable that the bevels 34 are tilted in a direction perpendicular to the direction of travel of the cuvette, but this is not essential.

In the described embodiment, the code embodied in facets 34 is read from a single side or flange of the cuvette. The bevels on each of the two flanges 30 extending from each side of the cuvette are formed symmetrically so that the same code will be read out independant of the orientation of the cuvette. Alternately, different codes could be provided on the different flanges to increase the number of possible codes.

The codes on facets 34 are not easily determined visually by a person. It is preferable that cuvettes having different codes be formed of a plastic material which is tinted in different colors corresponding to the different codes.

In the preferred embodiment, bevels 34 are approximately 0.125 inches wide on each side as shown by dimension B in FIG. 4. The full thickness of flange 30, as shown at A in FIG. 4, is 0.035 inches, and the bevels are formed at an angle of approximately 11 degrees with the horizontal top surface of the flange. The thickness of the flange through the thinnest part of bevels 34, as indicated by dimension C in FIG. 4, is 0.010 inches. These dimensions provide sufficient refraction of a light beam to allow the code embodied in the facets to be easily read by a light beam and photo detector, as described in more detail below. These dimensions are not critical, however, and other dimensions may be used.

Figure 7:
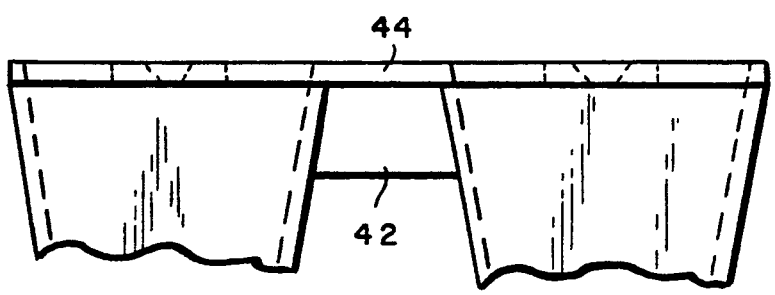
FIG. 7 is a partial side view of a double cuvette.

Referring to FIG. 6, there is shown a second embodiment of the invention which includes a double cuvette 38. Two receptacles 12 of similar dimensions to the receptacle in the cuvette of FIG. 1 are provided by the double cuvette of FIG. 6. The two receptacles 12 are connected by a horizontal portion 44 flush with the tops of the side walls 18 of the trapezoidal upper section of each cuvette. Flanges 30 extend the length of the double cuvette and provide further structural support between the Two cuvettes. A top web section 42 is formed coplanar with the side walls 18 of each of the receptacles 12 and extends downwardly for a distance of approximate 0.10 inches, as shown in FIG. 7.

The double cuvette shown in FIG. 6 has four locating holes 32 formed in side flanges 30. The configuration of these holes is similar to that of locating holes 32 discussed above in conjunction with FIG. 1. Each flange 30 has 6 facets 34, three adjacent to each receptacle 12. In the described embodiment, the two sets of three facets are separated by an opening 40 extending completely through flange 30. Alternately, an additional facet could be provided in the flange. Other numbers of facets may be used. The double cuvette of FIG. 6 is otherwise similar to the single cuvette of FIG. 1.

It is contemplated that both single and double cuvettes as shown in FIGS. 1 and 6, may be used in the same testing instrument intermixed. In the described embodiment, the first three facets detected as the cuvette is moved through the test instrument are used to encode the test to be performed, and a particular code is encoded in the second three facets 34 of a double cuvette to indicate to the instrument that a double cuvette is present. In the described embodiment, the double cuvette of FIG. 6 has the codes of facets 34 on opposite sides symmetrically arranged so that the cuvette appears identical to the machine when reversed 180 degrees.

Figures 8A, 8B, 8C:
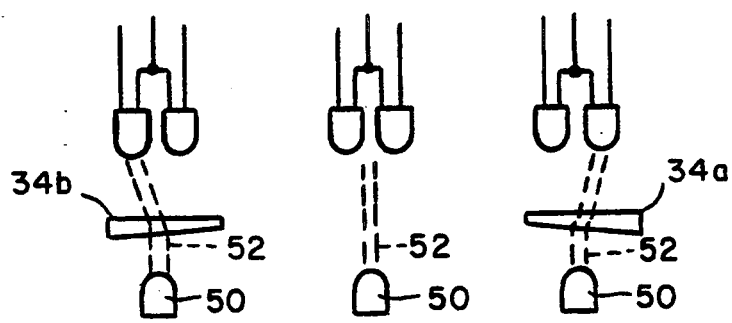
FIGS. 8A–8C illustrate how the facets may be decoded by a differential photodiode system.

FIGS. 8A-8C show schematically how the codes on the facets may be read. In these figures, a light source 50 directs a light beam 52 in a vertical direction. Two photodiodes 54 are arranged symmetrically on either side of the light beam 52. In the absence of a facet between light source 50 and photodiodes 54, the light shines equally on both of the photodiodes, as shown in FIG. 8B. As described below, the output of the photodiodes may be electrically balanced to provide equal outputs when a bevel is not present. If a bevel of one orientation is placed between the light source and photodiodes, light beam 52 is directed towards one of the photodiodes. In FIG. 8A, bevel 34b refracts the light beam 52 toward the left to illuminate the left hand photodiode. In FIG. 8C, an opposite bevel 34B refracts the light beam to the right illuminating the right hand photodiode. In this manner, the code embodied in the facets 34 of the cuvette may be detected. Light source 50 may be implemented in different ways. In the described embodiment, the light is provided by means of an infrared LED at the end of a small optical fiber in the small area along side the path of travel of the cuvette to the instrument. Photodiodes 54 are implemented by means of a differential diode pair such as a Siemens BPX48. The differential diode pair provides two matched photodiodes which are physically aligned and closely spaced.

Figure 9:
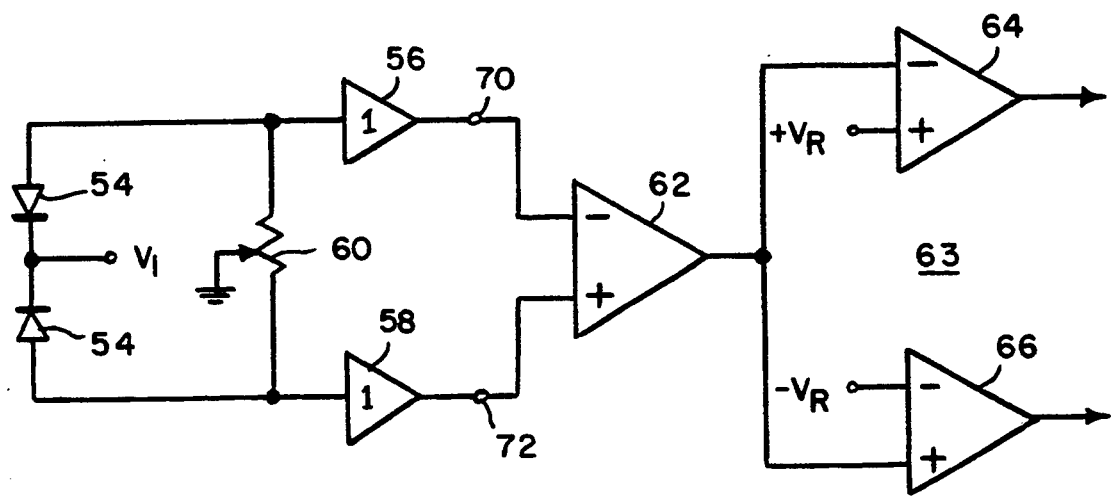
FIG. 9 illustrates a circuit for processing differential diode signals.

FIG. 9 shows one circuit suitable for reading the output from the photodiodes shown in FIG. 8. In FIG. 9, a voltage $V_1$ is applied To the common connection of differential diodes 54. The second terminals of each of the diodes 54 are applied to the inputs of respective unity-gain buffer amplifier 56 and 58. A potentiometer 60 is connected between diodes 54 with its wiper connected to ground. By adjusting potentiometer 60, the outputs from the diodes may be precisely matched.

The outputs from buffer amplifiers 56 and 58 are applied to the inputs of a differential amplifier 62. Differential amplifier has a gain of approximately 1000. When there is no bevel between light source 50 and photodiodes 54, the inputs to differential amplifier 62 will be equal providing a low output signal. When a facet 34 intersects light beam 52 and one or the other diodes, the inputs to differential amplifier 62 become unequal. The output of amplifier 62 then goes to a large positive or negative value to provide an indication of which diode has been illuminated. By detecting the output from the diodes in this manner, the effect of various error sources is reduced. Variations in the intensity of light from light source 50, contamination of the flanges and small differences in the transmissivity of the plastic material may result in changes in the absolute amount of light impinging on the diodes. By using the differential system shown, the effects of these variations are minimized to provide maximum accuracy for the reading of the values encoded by the bevels 34.

The output from differential amplifier 62 goes to a window comparator circuit 63, which provides three windows. The output from amplifier 62 is applied to the inverting and non-inverting inputs of two comparator circuits 64 and 66 respectively. Comparator 64 has a positive reference voltage, $+V_R$, applied to its non-inverting input; and comparator 66 has a negative reference voltage $-V_R$, applied to its inverting input.

The window comparator 63 provides three windows. Very low outputs from differential amplifier 62 result in low outputs from both comparators, indicating the absence of a bevel in light path 52. When the output from differential amplifier 62 goes high or low by more than a small amount, the corresponding comparator circuit provides a high output indicating the presence of the corresponding bevel in the light path 52.

Figure 10:
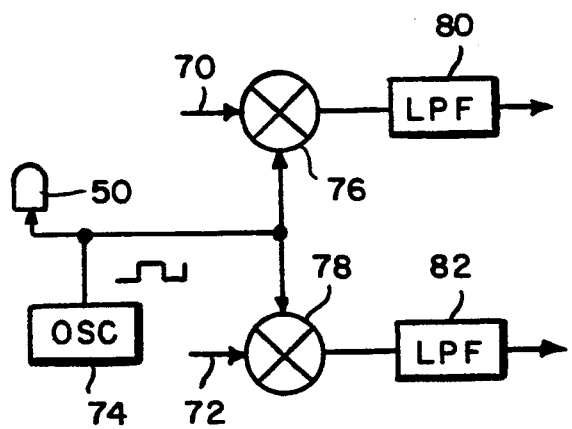
FIG. 10 shows circuitry for synchronously modulating and demodulating the light beam.

Preferably, the area in which light source 50 and photodiodes 54 detect the presence and orientation of bevels 34 is shielded from external light sources. Additional protection from variations in the output from photodiodes 54 caused by extraneous light may be provided by modulating the output of light source 50 and synchronously demodulating the signals from the photo detectors. FIG. 10 shows one circuit which can be added to circuitry of FIG. 9 for performing this function.

In FIG. 10, an oscillator 74 provides the square wave output signal. The oscillator output is applied to light source 50. In response, light source 50 provides pulses of light during alternate half cycles of the oscillator output signal. The signal from oscillator 74 is also applied to two multiplier circuits 76 and 78. Multiplier circuits 76 and 78 are inserted in series with the output signals from buffer amplifiers 56 and 58 in FIG. 9. Thus, multiplier 76 would be inserted at .70, and multiplier 78 would be inserted at point 72 in the FIG. 9 circuitry. In response to the output from oscillator 74, multipliers 76 and 78 multiply the signals on lines 70 and 72 by plus and minus 1 during alternate half cycles. The output signals from multipliers 76 and 78 are applied to low pass filters and 80 and 82 which serve to attenuate signal components at the frequency of oscillator 74 in the output from the multiplier circuits. Ambient light falling on either of the photodiodes 74 will produce a steady state signal which averages to zero when multiplied by the oscillator signal in the multiplier circuits. Illumination from light source 50 is synchronously detected by the multiplier circuits and will provide an output level at the output of low pass filters 80 and 82 representative of the level of light detected by the photodiode from light source 50.

Figure 11:
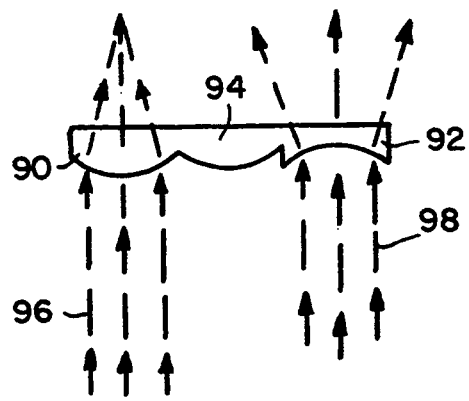
FIG. 11 illustrates how cylindrical lenses may be used to alternately encode a cuvette.

In the cuvettes described above, facets 34 were implemented by means of bevels which refract the light in one direction or another to encode the cuvettes. Alternately, the facets may be molded as cylindrical convex and concave lenses. This is shown in FIG. 11 where 3 cylindrical lenses 90, 92, and 94 are shown. Convex lenses 90 and 94 when placed in a light beam will focus the light beam and increase the intensity, as shown by arrows 96. By placing the light source at the focal point of the lenses 90 and 94, the increase of intensity can be maximized. Convex lens 92 causes the light beam to be diffused rather than focused, as shown by arrows 98. By using cylindrical lenses such as shown in FIG. 11 for the facets 34 of cuvettes described above, the encoding may be decoded by using a single photo detector which responds to variations in the magnitude of illumination produced by the cylindrical lenses of FIG. 11.

There has been described above by way of example a new design for a cuvette which includes a novel method of encoding cuvettes which may be detected by means of a light beam in an automatic testing apparatus. In applying the invention to different applications, modifications may be made to the embodiments described above to illustrate the principles of the invention. Accordingly, the invention should not be limited by the above description of such examples, but should be interpreted only in accordance with the following claims.

What is claimed is:

1. Apparatus for use with an object which travels along a predetermined path, said apparatus including:
  a light source for providing a light beam;
  means for detecting light from the light source and for providing an output signal representative thereof;
  a flange made of a transparent material and attached to the object so as to pass between the light source and the detecting means as the object travels along its path, the flange including:
  at least one encoding element for refracting light from the light source to said means for detecting so as to provide a photo-optically detectable code for the object, each encoding element refracting light in a different direction for each code state of the element, light being unrefracted if no element is present; and
  wherein said means for detecting includes a separate light detecting element for each of said code states, light being refracted to the detecting element by an encoding element in the corresponding code state.

2. The apparatus of claim 1 wherein the flange has one surface thereof which is substantially flat; and
  wherein each encoding element includes a selectively angled bevel formed on the surface opposite the flat surface so as to cause light passing through the bevel to be refracted.

3. The apparatus of claim 2 including a plurality of said bevels adjacent to one another and having one of two complementary angles with respect to the flange flat surface, whereby each bevel provides one bit of a binary code.

4. The apparatus of claim 3 wherein the means for detecting comprises:
  two light-detecting elements located with respect to the light source so as to be equally illuminated by the light beam in the absence of a said object between the light source and the detecting means and positioned so that the light beam is deflected by the bevels so that the light beam is refracted when it passes through said bevels;
  means responsive to output signals from the light detecting elements for providing and intermediate signal representative of the differential between the light-detecting elements output signals; and
  means responsive to the intermediate signal for providing three outputs representative of the absence of a bevel, the presence of a bevel having the first angle, or the presence of a bevel having the second angle between the light source and the detecting means 5. The apparatus of claim 4 further comprising;
  an oscillator which provides a periodic output signal;
  means for applying the oscillator output signal to the light source so as to cause the light source to turn on and off;
  means, responsive to the oscillator output signal, for demodulating the output signal from the detecting means synchronously with said light source; and
  means for filtering the demodulating means output signal to filter out signal not resulting from said light source.

6. The apparatus of claim 1 wherein the each encoding element is a cylindrical lens which is convex or concave in shape so as to focus or diffuse a light beam passing therethrough.

7. The apparatus of claim 6 wherein the detecting means includes means responsive to magnitude of the light from the light source for providing an intermediate signal representative thereof; and 8. The apparatus of claim 7 further comprising:
  an oscillator which provides a periodic output signal;
  means for applying the oscillator output signal to the light source so as to cause the light source to turn on and off;
  means, responsive to the oscillator output signal, for demodulating the output signal from the detecting means synchronously with said light source; and
  means for filtering the demodulating means output signal to filter out signal not resulting from said light source.

9. The apparatus of claim 1 wherein the transparent material is tinted a color which corresponds to the code, whereby a person may distinguish objects having different codes by means of their color.

10. An optically encoded object comprising:

an encoding area formed as part of said object, at least said area of the object being formed of a material which is substantially transparent to light, said area being adapted to be passed adjacent to a light source, and at least one bevel formed in said area, each of said at least one bevel being selectively angled to selectively refract light passed through said area from said source, selected bevel angles and selective refracting of light being in accordance with a predetermined code.

11. The object of claim 10 wherein said area has a surface of a selected shape, and wherein there are a plurality of said bevels formed adjacent to one another on said surface, each of said bevels having one of at least two different angles with respect to said surface, each bevel providing one bit of the code.

12. The object of claim 11 wherein each bevel has one of two complementary angles, the predetermined code being a binary code.

13. An optically encoded object comprising:

an encoding area formed as part of said object, at least said area of the object being formed of a material which is substantially transparent to light, said area being adapted to be passed adjacent to a light source, and one or more cylindrical lenses formed in said area, each of which lenses are convex or concave in shape so as to focus or diffuse a light beam passing therethrough in accordance with a predetermined code.

14. Apparatus for use with an object which travels along a predetermined path the apparatus comprising:

a light source for providing a light beam;

an encoding area formed as part of said object, at least said area of the object being formed of a material which is substantially transparent to light, and at least one bevel formed in said area, each of said at least one bevel being selectively angled so as to selectively refract light from said light source when passed therethrough, selective bevel angles and selective refracting of light being in accordance with a predetermined code;

and a separate light-detecting element for each angle at which a bevel may be selectively angled in accordance with said predetermined code, each detecting element being positioned relative to said light source such that the light beam is refracted to impinge on the detecting element by a bevel when the bevel is encoded to be at the corresponding angle.

15. The apparatus of claim 14 further comprising:

an oscillator which provides a periodic output signal;

means for applying the oscillator output signal to the light source so as to cause the light source to turn on and off;

means, responsive to the oscillator output signal, for demodulating the output signal from the detecting elements synchronously with said light source; and means for filtering the demodulating means output signal to filter out signal not resulting from said light source.

* * * * *